United States Patent [19]

Dubs et al.

[11] 4,237,290

[45] Dec. 2, 1980

[54] PROCESS FOR MAKING ASYMMETRICAL DISULFIDES

[75] Inventors: Paul Dubs, Zug; Heiner Küntzel, Dübendorf, both of Switzerland

[73] Assignee: Givaudan Corporation, Clifton, N.J.

[21] Appl. No.: 906,524

[22] Filed: May 16, 1978

Related U.S. Application Data

[62] Division of Ser. No. 726,100, Sep. 24, 1976, Pat. No. 4,130,562.

[30] Foreign Application Priority Data

Oct. 1, 1975 [CH] Switzerland .................. 12728/75
Jul. 20, 1976 [CH] Switzerland .................. 9280/76

[51] Int. Cl.³ .................. C07D 277/16; C07D 241/18
[52] U.S. Cl. .................. 544/335; 544/336; 548/146; 548/215; 546/339; 548/342; 586/25; 549/62; 549/66
[58] Field of Search .................. 544/298, 335, 336; 260/608, 247.2; 548/146, 215, 342; 546/339

[56] References Cited

U.S. PATENT DOCUMENTS 3,205,268  9/1965  Rosenwald .................. 260/608
3,859,297  1/1975  Sullivan .................. 260/302 S

FOREIGN PATENT DOCUMENTS 1252365  11/1971  United Kingdom .
1252366  11/1971  United Kingdom .

OTHER PUBLICATIONS

Reid, Organic Chemistry of Divalent Sulfur, pp. 362-369 (1960), vol. III, Chemical Publishing Co.

*Primary Examiner*—Nicholas S. Rizzo
*Attorney, Agent, or Firm*—Robert F. Tavares; Thomas Cifelli, Jr.

[57] ABSTRACT

Novel odorant and/or flavoring substances such as 2-phenylethyl-ethyl-disulphide, process for preparing such disulphides and odorant and flavoring products containing the sulphides are disclosed.

1 Claim, No Drawings

PROCESS FOR MAKING ASYMMETRICAL DISULFIDES

This is a division, of application Ser. No. 726,100 filed Sept. 24, 1976 now U.S. Pat. No. 4,130,562.

FIELD OF THE INVENTION

This invention relates to novel disulphides and to the fields of olfactory and flavoring products.

SUMMARY OF THE INVENTION

The novel disulphides of this invention have the formula:

$$R_1-(Y)_n-S-S-R_2 \tag{I}$$

wherein $R_1$ represents an optionally substituted phenyl or furyl group, or an optionally substituted monocyclic group containing nitrogen and/or sulphur and, if desired, also oxygen as the hetero atom, $R_2$ represents a lower alkyl or lower alkenyl group, Y represents an optionally mono- or di-substituted methylene group and n stands for 0-5 with the proviso that n stands for 2-5 when $R_1$ represents a phenyl or furyl group.

DESCRIPTION OF THE PREFERRED EMBODIMENTS

According to the process provided by the present invention, the disulphides of formula I hereinbefore are manufactured by reacting a compound of the general formula $$\begin{array}{c} A-S-N-NH-COOR \\ | \\ COOR \end{array} \tag{II}$$

or $$A-S-SCN \tag{III}$$

or $$\begin{array}{c} S \\ \| \\ A-S-S-COCH_3 \end{array} \tag{IV}$$

or $$A-S-S-A \tag{V}$$

or

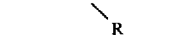 (VI)

or

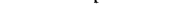 (VII)

with a mercaptan of the general formula $$A\text{-SH} \tag{VIII}$$

, whereby in the one reaction component A represents a group $R_1(Y)_n$ and in the other reaction component A represents a group $R_2$, Y and n have the significance given earlier except that n should only stand for 1-4 in formulae II, III and V, R represents a lower alkyl group, X represents the diacyl residue of an aliphatic or aromatic dicarboxylic acid and $Z^\ominus$ represents an anion.

As heterocyclic groups containing nitrogen and/or sulphur and, if desired, also oxygen as the hetero atom there come into consideration, in particular, 5-membered or 6-membered hetercyclic groups which contain one or more nitrogen atoms and/or one or more sulphur atoms. Examples of heterocycles forming a basis for these heterocyclic groups include pyrrole, pyridine, pyrazine, imidazole, pyrazole, pyrimidine, thiophene, thiazole, isothiazole, oxazole, triazole, etc, which heterocycles can be substituted (e.g. lower alkyl substituted).

The position at which the heterocycilc ring is bound with the rest of the molecule is not critical. The lower alkyl and lower alkenyl groups denoted by $R_2$ (or R as the case may be) are especially straight-chain or branched-chain groups containing from 1 to 6 carbon atoms (e.g. methyl, ethyl, propyl, isopropyl, butyl, sec.-butyl, isobutyl, amyl, hexyl, etc).

Y represents an optionally mono- or di-substituted methylene group. Indeed, in addition to the unsubstituted methylene group ($-CH_2-$), Y represents, in particular, a group of the formulae $$-CHR°-, \text{ or } -CR°R°°-$$

wherein R° and R°° represent lower alkyl or lower alkenyl groups.

The reaction of a compound of formula II with a mercaptan of formula VIII can be carried out according to methods known per se; for example: in accordance with Mukajyama et al, Tetrahedron Letters (1968), 5907 or Boekelheide et al, Tetrahedron Letters (1970), 1203.

The reaction is conveniently carried out in the presence of a base. Especially suitable bases are weak inorganic bases (e.g. ammonia, sodium bicarbonate, sodium carbonate, etc) or inorganic bases (e.g. aliphatic or aromatic amines). An especially preferred amine is N,N-diisopropylethylamine. The reaction can be carried out in the presence or absence of an organic solvent. Suitable solvents are hydrocarbons, especially aromatic hydrocarbons such as benzene, toluene etc, halogenohydrocarbons such as chloroform, dichloromethane etc, ethers such as diethyl ether, alcohols such as alkanols (e.g. methanol, ethanol etc), esters such as alkanecarboxylic acid esters (e.g. ethyl acetate). The temperature at which the reaction is carried out is not critical. The reaction is conveniently carried out at a temperature between about $-20°$ C. and the reflux temperature of the reaction mixture, preferably at approximately $20°-70°$ C.

The isolation of the reaction product from the reaction mixture can be carried out according to methods known per se, for example, by concentrating the reaction mixture, taking-up the residue in an organic solvent (e.g. an optionally chlorinated hydrocarbon, an ether or an ester etc), washing the organic phase with saturated aqueous sodium bicarbonate solution, drying the organic phase and concentrating same. The desired disulphide of formula I can be obtained in pure form by distillation or chromatography (e.g. on silica gel).

The compounds of formula II are conveniently prepared by reacting an azidocarboxylic acid ester of the general formula $$ROOC-N=N-COOR \tag{IX}$$

, wherein R has the significance given earlier, with a corresponding mercaptan of formula VIII. This reaction is preferably carried out in the presence of catalytic amounts of a strong acid such as a mineral acid (e.g. sulphuric acid or hydrochloric acid) or p-toluenesulphonic acid. This reaction is conveniently carried out in an inert solvent. Suitable solvents include hydrocarbons (e.g. hexane), aromatic hydrocarbons (e.g. benzene), halogenohydrocarbons (e.g. chloroform, dichloromethane etc) and ethers (e.g. diethyl ether). The temperature at which the reaction is carried out is not critical, but it conveniently lies between approximately −20° C. and 100° C. and preferably between room temperature and the reflux temperature of the solvent. A thus-obtained compound of formula II can subsequently be isolated according to methods known per se; for example, the methods described earlier. A compound of formula II can, however, also be reacted is situ with a mercaptan of formula VIII.

The reaction of a compound of formula III with a mercaptan of formula VIII can also be carried out according to methods known per se (Meijer et al, Rec.-Trav.Chim. Pays Bas 93, 242 (1974)). In this case, the mercaptan is conveniently used in the form of a metal salt (e.g. an alkali metal salt and especially the lithium salt). Moreover, the reaction is conveniently carried out in a solvating medium (e.g. an ether such as diethyl ether, dimethoxyethane etc, dimethylsulphoxide, dimethylformamide, hexamethylphosphortriamide etc). Dimethoxyethane is a preferred solvent. The temperature at which the reaction is carried out is not critical, but it conveniently lies between approximately −50° C. and approximately +50° C. and preferably between approximately −20° C. and room temperature. The desired disulphide of formula I obtained can be purified and isolated according to methods known per se, for example, according to one of the methods described earlier.

The compounds of formula III can be prepared by reacting a corresponding mercaptan of formula VIII with dirhodan. A mercaptan of formula VIII is conveniently reacted with dirhodan which is conveniently generated in situ. The dirhodan is conveniently obtained from a heavy metal rhodanide (e.g. lead rhodanide) by treatment with an oxidising agent (e.g. bromine, etc) in an inert solvent. Suitable solvents are hydrocarbons (e.g. the aforementioned) or ethers (e.g. the aforementioned). The temperature at which the reaction between a mercaptan of formula VIII and dirhodan is carried out is not critical, but it conveniently lies between about −30° C. and 80° C. and preferably between about −20° C. and room temperature. The thus-obtained compound of formula III can be isolated according to methods known per se; for example, the aforementioned methods. However, it can also be reacted in situ with a mercaptan of formula VIII.

For the reaction of a compound of formula IV with a mercaptan of formula VIII, a compound of formula IV is preferably first prepared in situ, namely from dimethyldithiobis(thioformate) of fomula X (E. I. Stout et al., J.Org.Chem.39, 562 (1974)) and a corresponding mercaptan of formula VIII:

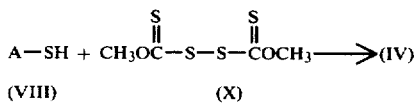

In practice, dimethyldithiobis(thioformate) of formula X is placed, for example, in an inert solvent at a temperature of, for example, −30° C. to room temperature, and the first mercaptan of formula VIII is added dropwise thereto. This dropwise addition is accompanied by the addition of an equivalent of a base (e.g. an organic base such as an amine, preferably pyridine). Conveniently, the dissolved, neutralised mercaptan is added dropwise. After completion of the reaction (e.g. after 5 to 30 minutes), the second mercaptan of formula VIII is added dropwise together with a second equivalent of base in the same manner as described earlier and is thus brought to reaction with the compound of formula IV.

The reaction mixture is conveniently worked-up by extraction with an organic solvent (e.g. one of the aforementioned solvents) or, in the case of strongly volatile disulphides of formula I (e.g. those having a boiling point of ca 100° C. or above) by simple concentration. The subsequent purification can be carried out according to methods known per se; for example, the methods mentioned earlier.

The reaction of a compound of formula V with a mercaptan of formula VIII involves the oxidation of the mercaptan of formula VIII by the compound of formula V (Reid, Organic Chemistry of bivalent Sulphur III, 372 (1960)). The reaction is conveniently carried out in the presence of a catalyst. As the catalysts there come into consideration, in particular, bases; for example, inorganic bases such as alkali metal hydroxides (e.g. sodium hydroxide or potassium hydroxide) and metal hydrides (e.g. sodium hydride) or organic bases such as aliphatic or aromatic amines (e.g. triethylamine, pyridine, etc). The reaction can be carried out in the presence of absence of a solvent. As the solvent, there may be mentioned, for example, one of the aforementioned solvents. The reaction is conveniently carried out at an elevated temperature. The reaction can be brought to completion by various measures; for example, by using excess of the compound of formula V, or, if desired, by continuous removal of the disulphide of formula I, or by continuous removal of the free mercaptan formed during the reaction, the removal being carried out, for example, by distillation. The working-up of the reaction mixture is conveniently carried out by removal (e.g. filtration) or neutralisation of the catalyst with acid and concentration of the crude product. Thereafter, the product can be recovered according to methods known per se.

The reaction of a compound of formula VI with a mercaptan of formula VIII can be carried out according to methods known per se; see, for example, K. s. Boustani et al, Tetrahedron Letters 1970 (3547); D. N. Harpp et al, Tetrahedron Letters 1970 (3551) or D. N. Harpp et al, J.Org.Chem.36, 3828 (1971), Buchel et al, Chem. Ber. 100, 1248 (1967), Behforouz et al, J.Org.Chem.34, 51 (1969).

The diacyl residue of an aliphatic or aromatic dicarboxylic acid denoted by X in formula VI can be, for example, the residue of glutaric acid, succinic acid, phthalic acid, etc.

The reaction is conveniently carried out using approximately equivalent amounts of the mercaptan of formula VIII and the compound of formula VI. The reaction can be carried out in an inert organic solvent; for example, a hydrocarbon such as an aliphatic hydrocarbon (e.g. hexane) or an aromatic hydrocarbon (e.g. benzene, etc), a chlorinated hydrocarbon (e.g. methylene chloride) and the like. The temperature at which the reaction is carried out is not critical, but it conveniently lies between about 0° C. and 150° C. and preferably between approximately room temperature and the reflux temperature of the reaction mixture.

For the reaction of a compound of formula VII with a mercaptan of formula VIII, the former is perferably prepared in situ. For this purpose, a—preferably symmetric—disulphide of the formula A—S—S—A is first treated with an appropriate alkylating agent. Examples of the alkylating agents which may be used are tri(lower alkyl)oxonium salts such as, in particular, the tetrafluoroborate. Other suitable salts can have, as the anion, the hexachloroantimonate, perchlorate, nitrate, arylsulphonate, alkylsulphonate or like anion. In order to obtain optimal yields, it is essential that the anion $Z^\ominus$ of the alkylating agent used reacts less rapidly with the cation of formula VII than the anion $A-S^\ominus$ of the mercaptan VIII does.

The reaction is conveniently carried out in an inert solvent; for example, an aliphatic or aromatic hydrocarbon such as hexane, heptane, benzene, toluene, etc, a chlorinated hydrocarbon such as chloroform, dichloromethane, etc, a nitro compound such as a nitroalkane (e.g. nitromethane, nitroethane, etc) or a sulphoxide (e.g. dimethylsulphoxide, etc). Preferred solvents are chlorinated hydrocarbons such as dichloromethane or nitro compounds such as nitromethane. The molar ratio of disulphide to alkylating agent preferably amounts to 1:1, but an excess of the disulphide can also be used.

The temperature at which the reaction is carried out is not critical, but it conveniently lies between about $-20°$ C. and $50°$ C. The reaction may, however, also be carried out at a higher or lower temperature. When nitromethane is used as the solvent, a temperature of ca $0°$ C. is preferred. The alkylated disulphide can be isolated, but it is conveniently reacted in situ with a mercaptan of formula VIII. The latter is preferably added to the dissolved salt as such or in the form of a salt (e.g. as the ammonium, alkali metal or alkaline earth metal salt) in one of the aforementioned solvents, especially nitromethane. The temperature at which this procedure is carried out is conveniently the temperature mentioned earlier.

The working-up of the reaction mixture can be carried out according to the methods described earlier (e.g. chromatography and/or distillation).

The starting materials used in the various procedures described earlier are either known or can be prepared according to methods known per se.

The disulphides of formula I hereinbefore possess particular odorant and/or flavouring properties. In particular, the flavouring spectrum is very broad. The present disulphides have fruity, spicy (e.g. mustard-like), vegetable-like (e.g. leek, celery, cauliflower, chive, onions, etc) and mushroom-like notes as well as cheese and meat notes. Of particular interest are the roast and meat notes.

The disulphides of formula I can accordingly be used, for example, for the perfuming of flavouring of products such as cosmetics (soaps, salves, powders, etc), detergents, foodstuffs, luxury goods and drinks, the disulphides preferably not being used alone but rather in the form of compositions containing other odorant or flavouring substances.

The present invention is thus concerned, in another aspect, with odorant and/or flavouring compositions which contain as an essential odour—and/or flavour imparting ingredient a dipeptide of formula I hereinbefore. Further, the present invention is concerned with a method of imparting an odour and/or a flavour to materials, which method comprises applying to said materials or incorporating therein an odour—and/or flavour-imparting amount of a disulphide of formula I hereinbefore or of an odorant and/or flavouring composition as hereinbefore defined.

Having regard to their natural notes, the present disulphides are especially suitable for the modification of known compositions (e.g. those of the Chypre type or of flower notes).

The concentration of the disulphides of formula I in the composition of this invention can vary within wide limits depending on the purpose of use. For example, the concentration can be between about 0.001 wt.% in the case of detergents, and about 10 wt.% in the case of alcoholic solutions. in perfume bases or concentrates, the concentrations can, of course, also be higher.

The disulphides of formula I can be used as flavouring substances, for example, for the production or improvement, intensification, enhancement or modification of fruit, meat, or roast notes in foodstuffs (meat, synthetic meat products, sauces, broths, soups, vegetables, seasoning agents, snack foods, roast products such as coffee or cocoa, milk products such as cheese, curd, yoghurt, etc), in luxury goods (tobacco, crackers etc) and drinks (lemonades etc).

The pronounced flavour qualities of the present disulphides enable them to be used in low concentrations. A suitable range is ca 0.001 ppm–10 ppm, preferably ca 0.1 ppm–10 ppm. in the finished product (i.e. the aromatised foodstuff, luxury goods or drink).

The disulphides of formula I can be mixed with the ingredients used for flavouring substance compositions or can be added to such aromas in the usual manner. Among the aromas contemplated in accordance with the present invention there are to be understood flavouring substance compositions which can be diluted or dispersed in edible materials in a manner known per se. They can be converted according to methods known per se in the usual forms of use such as solutions, pastes or powders. The products can also be spray-dried, vacuum-dried or lyophilised.

As carrier materials, thickening agents, flavour-improvers, spices and auxiliary ingredients and the like which are suitable in the production of such customary forms of use, there may be mentioned, for example:

Gum arabic, tragacanth, salts or brewers' yeast, alignates, carageens or similar absorbants; maltol, dienals, spice oleoresins, smoke flavours; cloves, diacetyl, sodium citrate; monosodium glutamate, disodium inosine-5'-monophosphate (IMP), disodium guanosine-5-phosphate (GMP); or special flavouring substances, water, ethanol, propyleneglycol, glycerine.

The following Examples illustrate the process provided by the present invention:

EXAMPLE 1

8.66 g (0.0429 mol) of azidocarboxylic acid diisopropyl ester are dissolved in 40 ml of chloroform. There are then added dropwise 6 g (0.0429 mol) of 2-(2-pyrazinylethyl)-mercaptan and thereafter 4 drops of concentrated sulphuric acid. The mixture is held at reflux temperature for 4 hours. The mixture is then left to cool to room temperature, treated with 20 ml of saturated sodium bicarbonate solution and the resulting mixture extracted four times with 50 ml of chloroform each time. The organic phases are combined, dried over anhydrous sodium sulphate and concentrated on a rotary evaporator at 40° C./12 mm Hg. The yield of crude N-[1'-thia-3'-pyrazin-2-yl-propyl]-N,N'-diisopropoxycarbonylhydrazine amounts to 16.6 g. The product has the following analytical data:

NMR(CDCl$_3$): 8.60–833 (m, 3H), 6.60 (s, broad, 1H), 5.22 (septet, J=6 Hz, 1H) 4.96 (septet, J=6 Hz, 1H), 3.15 (s, 4H), 1.43 (d,J=6 Hz, 6H), 1.27 (d, J=6 Hz, 6H) ppm.

IR (liq.): bands inter alia at 3350, 1730, 1240, 1105, 755 cm$^{-1}$.

The aforementioned hydrazine derivative is dissolved in 160 ml of isopropanol and treated with 7.5 g (1.2 mol equivalents) of diisopropylethylamine. The mixture is then cooled to 0° C. and excess methylmercaptan is passed through. After completion of the addition, the mixture is stirred for a further 2 hours. The mixture is extracted with 50 ml of saturated sodium bicarbonate solution and four times with 100 ml of chloroform each time. The combined organic phases are dried over anhydrous sodium sulphate and concentrated on a rotary evaporator at 40° C./12 mm Hg. The crude product obtained is chromatographed on a column of 150 g of silica gel using hexane/ether (1:4) for the elution. The fractions are combined and subjected to a short-path distillation in a bulb-tube. In this manner there are obtained 1.2 g of pure 2-(2-pyrazinylethyl)-methyl-disulphide.

$n_D^{20}$ = 1.5863; boiling point 85°–95°/0.035 mm Hg.

IR (liq.): bands inter alia at 1520, 1470, 1430, 1400, 1300, 1160, 1110, 1060, 1020, 850, 830 cm$^{-1}$.

Odour and flavour: sulphur-like, meaty, vegetable-like, (leek, chive, garlic, onions, cauliflower),

EXAMPLE 2

To 120 ml of diethyl ether, pre-cooled to 0° C., are added while stirring 3 ml of bromine and thereafter, under an argon atmosphere, 22.5 g (0.0696 mol) of crystalline lead rhodanide. The mixture is stirred until the colour of the bromine has disappeared completely, this requiring 2 hours. The mixture is then filtered from the lead salt and the filtrate cooled to −5° C. 7.0 g (0.05 mol) of 2-(2-pyrazinylethyl)-mercaptan dissolved in 30 ml of ether is added to the filtrate. After completion of the addition, the mixture is stirred for 15 minutes at 0° C. to −5° C., then poured on to ice and extracted four times with 50 ml of ether each time. The organic phases are combined, washed with 50 ml of water, dried over anhydrous sodium sulphate and concentrated on a rotary evaporator at 0°–20° C./12 mm Hg. The thus-obtained crude 2-(2-pyrazinyl)-ethylthiorhodanide (12 g) is immediately further processed. [IR bands (liq.) of the crude product 2080 cm$^{-1}$].

Methylmercaptan is passed into 60 ml of freshly distilled dimethoxyethane cooled to −20° C. 27.5 ml (110% relative to mercaptan) of a 2.8% n-butyllithium/hexane solution are added dropwise thereto, a white suspension forming. 12 g of the foregoing rhodanide dissolved in 50 ml of dimethoxyethane are now added dropwise at −20° C. to −30° C. The mixture is left to come to room temperature. The mixture is poured on to ice and extracted four times with 125 ml of ether each time. The organic phases are combined, dried over anhydrous sodium sulphate and concentrated on a rotary evaporator at 40° C./12 mm Hg. The crude product is chromatographed on 150 g of silica gel using hexane/ether (1:4) for the elution. The fractions are concentrated and subjected to a short-path distillation in a bulb-tube at 90°–92°/0.03 mm Hg. In this manner there are obtained 2.5 g (26.9% relative to the mercaptan used) of pure 2-(2-pyrazinylethyl)-methyl-disulphide.

$n_D^{20}$ = 1.5905.

EXAMPLE 3

(a) A solution of 8.15 g (0.055 mol) of trimethyloxonium tetrafluoroborate in 20 ml of nitromethane is added to a solution, cooled to 0° C., of 5.17 g (0.055 mol) of freshly distilled dimethyldisulphide in 10 ml of nitromethane. After completion of the addition, the mixture is stirred at this temperature for 90 minutes. There is now added dropwise thereto at 0° C. a solution of 7 g (0.05 mol) of 2-(2-pyrazinethyl)-mercaptan as well as 6.45 g (0.05 mol) of diisopropylamine in 10 ml of nitromethane. The mixture is left to come to room temperature, treated with 50 ml of saturated sodium bicarbonate solution and ice and the mixture extracted four times with 100 ml of chloroform each time. The organic phases are combined, dried over anhydrous sodium sulphate and then concentrated on a rotary evaporator at 40° C./12 mm Hg. The crude product obtained is chromatographed on 150 g of silica gel using hexane/ether (1:4) for the elution. The fractions are combined and subjected to a short-path distillation in a bulb-tube at 85°–88° C./0.03 mm Hg. There are obtained 4.25 g (45.7%) of pure 2-(2-pyrazinethyl)-methyl-disulphide.

According to the same procedure, from dimethyldisulphide and 1-(2-thiazolyl)-2-methylpropyl-mercaptan there is obtained [1-(2-thiazolyl)-2-methylpropyl]-methyl-disulphide.

$n_D^{20}$ = 1.5770.

IR (liq.): bands inter alia at 1500, 1470, 1430, 1420, 1390, 1370, 1195, 1140, 1055, 730 cm$^{-1}$.

Odour and flavour: earthy, fruity (cassis), sulphur-like, vegetable-like (celery).

From dimethyldisulphide and 2-mercapto-pyridine there is obtained 2-pyridyl-methyl-disulphide. $n_D^{20}$ = 1.6225. IR (liq.): bands inter alia at 1580, 1570, 1450, 1420, 1125, 770 730 cm$^{-1}$.

Odour and flavour: earthy, sulphur-like, green, vegetable-like (cauliflower, onion), after broad-leaved garlic, cheese.

From dimethyldisulphide and 2-mercapto-thiazole there is obtained 2-thiazolyl-methyl-disulphide. $n_D^{20}$ = 1.6408. IR (liq.): bands inter alia at 1485, 1390, 1310, 1060, 1050, 725 cm$^{-1}$.

Odour and flavour: roast note, sulphur-like, green, cabbage-, chive-like, meat-like (pork).

From dimethyldisulphide and 2-mercapto-pyrimidine there is obtained 2-pyrimidinyl-methyl-disulphide. $n_D^{20}$ = 1.6620. IR (liq.): bands inter alia at 1560, 1385, 1200, 1175, 785 cm$^{-1}$.

Odour and flavour: earthy, spicy, vegetable-like (cauliflower, kohlrabi), of cheese.

From dimethyldisulphide and 4,5-dimethyl-2-thiono-4-oxazoline there is obtained (4,5-dimethyl-2-oxazolyl)-methyldisulphide. $n_D^{20}$ = 1.5598. IR (liq.): bands inter alia at 2950, 1638, 1495, 1435, 1225, 1175, 1103, 950, 745 cm$^{-1}$.

Odour: spicy "Maggi". Flavour: spicy, chive-like, reminiscent of lightly fried mushrooms.

(b) A solution of 4.18 g (0.022 mol) of triethyloxonium tetrafluoroborate in 12 ml of nitromethane is added to a solution of 2.86 g (0.022 mol) of dimethyldisulphide in 8 ml of nitromethane (filtered over basic aluminium oxide) at reflux temperature. After completion of the addition, the mixture is stirred at 30°–40° C. for a further 2 hours. There is then added dropwise at 30° C. a mixture (two phases) of 2.22 g (0.02 mol) of 2-mercapto-pyridine and 2.58 g (0.02 mol) of diisopropylethylamine in 15 ml of nitromethane and the resulting mixture is stirred at ca 30°–40° C. for a further 2 hours.

The working-up is carried out as described in Example 3a). There are obtained 2.29 g (67% relative to 2-mercapto-pyridine) of pure 2-pyridyl-ethyl-disulphide. $n_D^{20} = 1.6059$. IR (liq.): bands inter alia at 1580, 1570, 1455, 1424, 1125, 775, 730 cm$^{-1}$.

Odour: sulphur-like, after onions, penetrating. Flavour: onion-like, sulphur-like, burning.

(c) From 3.3 g (0.022 mol) of dipropyldisulphide, 3.26 g (0.022 mol) of trimethyloxonium tetrafluoroborate, 2.22 g (0.02 mol) of 2-mercapto-pyridine and 2.58 g (0.02 mol) of diisopropylethylamine there is obtained, according to the procedure described in Example 3b), 2-pyridyl-propyl-disulphide. Yield: 2.65 g (71.6% relative to 2-mercapto-pyridine). $n_D^{20} = 1.5916$. IR (liq.): bands inter alia at 1580, 1570, 1450, 1420, 1125, 770, 730 cm$^{-1}$.

Odour: penetrating, sulphur-like, green, after chive. Flavour: sulphur-like, green, of chive.

(d) From 3.3 g (0.022 mol) of diisopropyldisulphide, 3.26 g (0.022 mol) of trimethyloxonium tetrafluoroborate, 2.24 g (0.02 mol) of 2-mercapto-pyrimidine and 2.58 g (0.02 mol) of diisopropyl-ethylamine there is obtained, according to the procedure described in Example 3b), 2-pyrimidinyl-isopropyl-disulphide.

Yield: 2.5 g (67.2% relative to 2-mercapto-pyrimidine).

$n_D^{20} = 1.5858$.

IR (liq.): bands inter alia at 1570, 1560, 1485, 1200, 1175, 1165, 1060, 785, 755 cm$^{-1}$.

Odour: penetrating, sharp, green, of onions.

Flavour: penetrating, burning, of onions.

(e) From 2.08 g (0.022 mol) of dimethyldisulphide, 4.18 g (0.022 mol) of triethyloxonium tetrafluoroborate, 2.24 g (0.02 mol) of 2-mercapto-pyrimidine and 2.58 g (0.02 mol) of diisopropyl-ethylamine there is obtained, according to the procedure described in Example 3b), 2-pyrimidinyl-methyl-disulphide:

Yield 1.8 g (57% relative to 2-mercapto-pyrimidine). $n_D^{20} = 1.6218$.

IR (liq.): bands inter alia at 1560, 1385, 1200, 1175, 785 cm$^{-1}$.

(f) From 2.68 g (0.022 mol) of diethyldisulphide, 3.26 g (0.022 mol) of trimethyloxonium tetrafluoroborate, 2.24 g (0.02 mol) of 2-mercapto-pyrimidine and 2.58 g (0.02 mol) of diisopropyl-ethylamine there is obtained, according to the procedure described in Example 3b), 2-pyrimidinyl-ethyl-disulphide.

Yield: 2.2 g (64% relative to 2-mercapto-pyrimidine). $n_D^{20} = 1.6025$.

IR (liq.): bands inter alia at 1570, 1555, 1385, 1200, 1175, 785, 755 cm$^{-1}$.

Odour: sulphur-like, of vegetables (boiled onions).

Flavour: sulphur-like, reminiscent of boiled onions.

EXAMPLE 4

5.65 g (0.483 mol) of 2-mercapto-thiazole and 10 g (0.483 mol) of N-ethylthiophthalimide are stirred at room temperature in 60 ml of benzene for 60 hours. The product is then filtered through paper and subsequently filtered over 15 g of silica gel. Upon concentration there is obtained a reddish-yellow product which is still liquid. High-vacuum distillation through a Vigreux column gives 6.65 g (75%) of a yellowish coloured product having the following data: boiling point 65°–66° C./0.03 mm Hg; $n_D^{20} = 1.6190$. This product is 2-thiazolyl-ethyl-disulphide having a purity of 95%.

IR (liq.): bands at 3120, 3000, 1485, 1390, 1260, 1155, 1060, 1040, 755, 725 cm$^{-1}$.

Odour and flavour: sulphur-like, roast-like, meat-like, vegetable-like (leek, onions, cabbage), of carrots.

According to the same procedure from 1-methyl-2-mercapto-imidazole and N-ethylthiophthalimide there is obtained 2-(1-methylimidazolyl)-ethyl-disulphide. $n_D^{20} = 1.5890$.

IR (liq.): bands at 3150, 3000, 1610, 1460, 1415, 1285, 1125, 920, 760, 695 cm$^{-1}$.

Odour and flavour: sulphur-like, roast-like, vegetable-like (leek, onions), of boiled eggs.

From 2-mercapto-thiazole and N-butylthiophthalimide there is obtained 2-thiazolyl-butyl-disulphide. $n_D^{20} = 1.5890$. IR (liq.): bands at 3120, 3000, 1485, 1390, 1310, 1060, 1045, 725 cm$^{-1}$.

Odour and flavour: sulphur-like, faintly green, spicy (garlic), sweet, vegetable-like (leek, onions, celery, chive), From 1-methyl-2-mercapto-imidazole and N-isopropylthiophthalimide there is obtained 2-(1-methylimidazolyl)-isopropyl-disulphide. $n_D^{20} = 1.5736$. IR (liq.): bands inter alia at 3130, 3000, 1505, 1455, 1285, 1015, 760, 695 cm$^{-1}$.

Odour and flavour: meat-like, roast-like, spicy, of onions, eggs.

Starting from thenylmercaptan and N-ethylthiophthalimide there is obtained ethyl-thenyl-disulphide. $n_D^{20} = 1.6044$. IR (liq.): bands inter alia at 3000, 1450, 1250, 1035, 850, 700 cm$^{-1}$;

Odour: penetrating, spicy, after garlic.

Flavour: spicy, of garlic.

Starting from thenylmercaptan and N-propylthiophthalimide there is obtained propyl-thenyl-disulphide. IR (liq.): bands inter alia at 2990, 1455, 1220, 1030, 850, 700 cm$^{-1}$.

Odour: spicy, green (chive).

Flavour: faintly spicy, earthy, green.

Starting from 1-methyl-2-mercapto-imidazole and N-propylthiophthalimide there is obtained 2-(1-methylimidazolyl)-propyl-disulphide. $n_D^{20} = 1.5756$. IR (liq.): bands inter alia at 3105, 2980, 1500, 1450, 1275, 1115, 1010, 750, 685 cm$^{-1}$.

Odour: sulphur-like, green, vegetable-like.

Flavour: sulphur-like, vegetable-like.

Starting from 2-mercapto-thiazole and N-isopropyl-thiophthalimide there is obtained 2-thiazolyl-isopropyl-disulphide. $n_D^{20} = 1.5984$. IR (liq.): bands inter alia at 3010, 1490, 1395, 1160, 1065, 1050, 730 cm$^{-1}$.

Odour: sulphur-like, faint roast note.

Flavour: sulphur-like, faint roast-note, burning.

Starting from 1-methyl-2-mercaptomethyl-pyrrole and N-ethylthiophthalimide there is obtained (1-methyl-2-pyrrolyl)-methyl-ethyl-disulphide. $n_D^{20} = 1.5816$. IR (liq.): bands inter alia at 3140, 3000, 1495, 1310, 1250, 1090, 720, cm$^{-1}$.

Odour: sweetish, green, sulphur-like (onion-like).

Flavour: sulphur-like (onion-like), sweet.

Starting from 4,5-dimethyl-2-thiono-4-oxazoline and N-ethylthiophthalimide there is obtained (4,5-dimethyl-2-oxazolyl)ethyl-disulphide. $n_D^{20} = 1.5467$. IR (liq.): bands inter alia at 3020, 2970, 1640, 1450, 1175, 1105, 950, 745 cm$^{-1}$.

Odour and flavour: spicy, "Maggi", mushroom-like.

Starting from 4-ethyl-2-thiono-4-oxazoline and N-ethylthiophthalimide there is obtained (4-ethyl-2-oxazolyl)ethyl-disulphide. $n_D^{20} = 1.5549$. IR (liq.):

bands inter alia at 3000, 2970, 1590, 1485, 1250, 1135, 1080, 950, 760 cm$^{-1}$.

Odour: spicy (lovage), slightly sulphurous, cheese-like.

Flavour: "Maggi", onion-like, reminiscent of fully matured cream cheese.

Starting from 4,5-dimethyl-2-thiono-4-oxazoline and N-propylthiophthalimide there is obtained (4,5-dimethyl-2-oxazolyl)propyl-disulphide. $n_D^{20} = 1.5321$. IR (liq.): bands inter alia at 2980, 1635, 1450, 1225, 1173, 1100, 945, 740 cm$^{-1}$.

Odour and flavour: slightly sulphurous, chive-like and broad-leaved garlic-like.

EXAMPLE 5

A mixture of 8.26 g (0.052 mol) of 2-(4-methyl-5-thiazolyl)-ethyl-mercaptan and 33.07 g (0.208 mol) of dimethyldisulphide is treated with 50 mg of sodium hydride (50% dispersion in oil) and the mixture is heated to reflux for 4 hours. The mixture is then left to cool, filtered over 10 g of aluminium oxide (activity I, neutral), which is back-washed with ether, and concentrated in a vacuum. The resulting crude product (9.5 g) is distilled through a Hempel column under a high vacuum, there being obtained 6.45 g of [2-(4-methyl-5-thiazolyl)ethyl]-methyl-disulphide. Boiling point 104°–110°/0.02 mm Hg; $n_D^{20} = 1.5944$; purity: 99%.

IR (liq.): bands inter alia at 3100, 2960, 1545, 1415, 1220, 955, 1005, 840, 795 cm$^{-1}$.

Odour: sulphur-like, spicy (mustard).

Flavour: sulphur-like, spicy, hot.

EXAMPLE 6

(a) 8 g (0.058 mol) of phenethylmercaptan are added with intensive stirring to a suspension of 12 g (0.058 mol) of N-ethylthiophthalimide in 70 ml of benzene. After a few minutes, a homogeneous solution forms and the phthalimide slowly begins to precipitate out therefrom. After stirring for 48 hours at room temperature, the mixture is filtered through a paper filter, the filtrate is concentrated in a vacuum and the crude 2-phenylethyl-ethyl-disulphide (12.8 g) obtained is distilled through a Vigreux column. There are thus obtained 10.5 g of pure product (91% of theory) which has a purity of 99% (gas-chromatographic estimation). Boiling point 87–88 mm Hg/0.04 mm Hg; $n_D^{20} = 1.5742$.

IR (liquid): bands inter alia at 3020, 1610, 1505, 1460, 1260, 710 cm$^{-1}$.

Odour: sulphur-like, spicy, sweetish.

Flavour: spicy, sweetish, somewhat sulphur-like.

(b) Starting from 5 g (0.033 mol) of 3-phenylpropyl-mercaptan and 6.65 g (0.033 mol) of N-ethylthiophthalimide there are obtained, according to the procedure described in Example 6a) and after distillation, 4.85 g of 3-phenylpropyl-ethyl-disulphide (purity 98%). Boiling point 90°–91°/0.04 mm Hg; $n_D^{20} = 1.5639$. IR (liquid): bands inter alia at 3080, 2980, 1950, 1605, 1700, 1455, 1250, 845, 805 cm$^{-1}$.

Odour : sulphur-like, green, vegetable-like;

Flavour: vegetable-like, sulphur-like, green.

(c) Starting from 5 g (0.028 mol) of 5-phenylpentyl-mercaptan and 5.62 g (0.028 mol) of N-ethylthiophthalimide there are obtained, according to the procedure described in Example 6a) and after filtration through silica gel (back-washing with hexane) and bulb-tube distillation, 2.98 g of 5-phenylpentyl-ethyl-disulphide (purity: 99%). Boiling point: 150°–180° C. (oven temperature)/0.02 mm Hg; $n_D^{20} = 1.5512$. IR (liquid): bands inter alia at 2930, 1950, 1600, 1590, 1445, 1250, 1025, 840, 795 cm$^{-1}$.

Odour: sulphur-like, green, flowery;

Flavour: flowery, green.

(d) Starting from 5.6 g (0.048 mol) of 2-furylethyl-mercaptan and 9.1 g (0.048 mol) of N-ethylthiophthalimide there are obtained, according to the procedure described in Example 6a) and after chromatography on 100 g of silica gel (elution with toluene), 2.38 g of ethyl-2-(2-furyl)-ethyl-disulphide (purity: 96%). $n_D^{20} = 1.5450$. IR (liquid): bands inter alia at 3000, 1600, 1505, 1150, 1010, 735 cm$^{-1}$.

Odour: sulphur-like, penetrating, after onions;

Flavour: sulphur-like, green, faintly flowery.

The following Examples illustrate typical odorant and/or flavouring compositions provided by the present invention:

EXAMPLE 7

A broth can be prepared as follows:

(A) 20.0 g in each case of a mixture A or B

|  | A | B |
|---|---|---|
|  | Parts by weight | |
| 2-Pyrimidinyl-methyl-disulphide | — | 0.5 |
| Diallyldisulphide | 60 | 60 |
| Allylmercaptan | 0.5 | 0.5 |
| Mustard oil synthetic | 2.5 | 2.5 |
| Dimethyldisulphide | 0.5 | — |
| 2,4-Decadienal (10% in ethyl alcohol) | 1 | 1 |
| Capric aldehyde | 0.1 | 0.1 |
| Maltol | 2.5 | 2.5 |
| Butyric acid (10% in ethyl alcohol) | 0.2 | 0.2 |
| Benzyl alcohol | 132.7 | 132.7 |
|  | 200.0 | 200.0 | are mixed with 1000 g of onion oil. At an amount of 20 g/100 l of broth the odour and flavour of the broth prepared using composition A are insipid, whereas the broth prepared using composition B possesses an excellent onion flavour.

(B) 20.0 g in each case of a mixture A or B

|  | A | B |
|---|---|---|
|  | Parts by weight | |
| 2(1-Methylimidazolyl)-ethyl-disulphide | — | 20 |
| Diallylsulphide | 60 | 40 |
| Allylmercaptan | 0.5 | 0.5 |
| Mustard oil synthetic | 2.5 | 2.5 |
| Dimethyldisulphide | 0.5 | 0.5 |
| 2,4 Decadienal (10% in ethyl alcohol) | 1.0 | 1.0 |
| Capric aldehyde | 0.1 | 0.1 |
| Maltol | 2.5 | 2.5 |
| Butyric acid (10% in ethyl alcohol) | 0.2 | 0.2 |
| Benzyl alcohol | 132.7 | 132.7 |
|  | 200.0 | 200.0 | are mixed with 1000 g of onion oil. At an amount of 20 g/100 l of broth the broth aromatised with composition A, a traditional aroma composition, possesses a metallic after-flavour as well as an unsatisfactory onion note. By the partial replacement of the diallyldisulphide by 2-(1-methylimidazolyl)-ethyl-disulphide (composition B) the aromatised broth takes on an agreeable sweetish note reminiscent of boiled onions.

(C) 20.0 g in each case of a mixture A or B

|  | A | B |
|---|---|---|
|  | Parts by weight | |
| 2-Pyridyl-ethyl-disulphide | — | 0.5 |
| Diallyldisulphide | 60 | 60 |
| Mustard oil synthetic | 2.5 | 2.5 |
| Dimethyldisulphide | 0.5 | — |
| Methylthiopropionic acid methyl ester | 0.5 | 0.5 |
| Leaf alcohol | 2.0 | 2.0 |
| Diacetyl (10% in ethanol) | 0.2 | 0.2 |
| Maltol | 2.0 | 2.0 |
| Benzyl alcohol | 132.3 | 132.3 |
|  | 200.0 | 200.0 | are mixed with 1000 g of onion oil. At an amount of 20 g/100 l of broth the odour and flavour of the broth prepared by using the composition A are insipid. The broth prepared using composition B possesses an excellent onion flavour. It is reminiscent of fresh onions, a faintly hot-burning note being noticed.

(D) 20.0 g in each case of a mixture A or B

|  | A | B |
|---|---|---|
|  | Parts by weight | |
| 2-Pyrimidinyl-ethyl-disulphide | — | 0.5 |
| Diallyldisulphide | 60 | 60 |
| Mustard oil synthetic | 2.5 | 2.5 |
| Dimethyldisulphide | 0.5 | — |
| Methylthiopropionic acid methyl ester | 0.5 | 0.5 |
| Leaf alcohol | 2.0 | 2.0 |
| Diacetyl (10% in ethanol) | 0.2 | 0.2 |
| Maltol | 2.0 | 2.0 |
| Benzyl alcohol | 132.3 | 132.3 |
|  | 200.0 | 200.0 | are mixed with 1000 g of onion oil. At an amount of 20 g/100 l of broth the odour and flavour of the broth prepared using composition A are insipid. Upon replacement of the dimethyldisulphide by 2-pyrimidinyl-ethyl-disulphide the onion flavour of the broth is advantageously altered with the same dosage of composition B, in that a faintly hot-burning note reminiscent of fresh onions sets in.

EXAMPLE 8

A brown meat sauce can be obtained as follows: 125.0 g of a mixture consisting of

|  | Parts by weight |
|---|---|
| Cooking salt | 8.00 |
| Monosodium glutamate | 2.67 |
| Sugar | 4.00 |
| HVP, Type 4 BE (hydrolysed vegetable proteins) | 6.40 |
| Onion powder | 1.84 |
| Caramel powder | 1.12 |
| Tomato powder | 5.33 |
| VEE-Cream (artificial cream on the basis of vegetable oils, spray dried) | 26.67 |
| Laurel, soluble | 0.04 |
| White pepper, soluble | 0.08 |
| Thyme, soluble | 0.04 |
| Marjoram, soluble | 0.04 |
| Nutmeg, soluble | 0.04 |
| Modified waxy maize corn starch (maize starch) | 18.67 |
| White flour | 25.06 |
|  | 100.00 | are stirred into 1 liter of cold water and boiled up while stirring continuously. After boiling for 3 minutes, the flavour of this brown meat sauce is initially insipid and not typical. After the addition of 2 ppm of 2-thiazolyl-methyl-disulphide, there is established an excellent meat flavour with a distinct roast onion-like, meat-like note.

EXAMPLE 9

An onion cream soup can be obtained as follows:
(A) 140.0 g of a mixture consisting of

|  | Parts by weight |
|---|---|
| Margarine | 28.70 |
| White flour | 18.61 |
| Dried onions | 12.52 |
| Skim milk powder | 12.52 |
| Carrot starch | 12.52 |
| Onion powder | 3.75 |
| Cooking salt | 8.75 |
| Monosodium glutamate | 1.25 |
| HVP (hydrolysed vegetable proteins) | 1.25 |
| White pepper, milled | 0.13 |
|  | 100.00 | are added to 1 liter of cold water, boild up and removed from the heat as soon as the pieces of onion are cooked. The flavour of this onion soup is insipid, not pronounced, and the flavour scarcely comes into play. By the addition of 2 ppm of [1-(2-thiazolyl-2-methyl-propyl)]-methyldisulphide the onion flavour present is enhanced in an advantageous manner. In addition, the soup takes on an agreeable vegetable-like, spicy note which is reminiscent of celery.

(B) 140.0 g of a mixture consisting of

|  | Parts by weight |
|---|---|
| Margarine | 28.70 |
| White flour | 18.61 |
| Dried onions | 12.52 |
| Skim milk powder | 12.52 |
| Carrot starch | 12.52 |
| Onion powder | 3.75 |
| Cooking salt | 8.75 |
| Monosodium glutamate | 1.25 |
| HVP (hydrolysed vegetable proteins) | 1.25 |
| White pepper, milled | 0.13 |
|  | 100.00 | are added to 1 liter of cold water, boiled up and removed from the heat as soon as the pieces of onion are cooked. The flavour of this onion soup is insipid, not very pronounced and the flavour comes into play only faintly. By the addition of 0.5 ppm of 2-thiazolyl-ethyl-disulphide the existing onion flavour is enhanced in an extremely advantageous manner in that a pronounced, pleasant roast onion note and a faint broth note appears.

EXAMPLE 10

A clear meat soup can be obtained as follows: 20.0 g of a mixture consisting of

|  | Parts by weight |
|---|---|
| Cooking salt | 50.00 |
| Monosodium glutamate | 20.04 |
| Caramel powder | 0.20 |
| Nutmeg, soluble | 0.06 |
| Clove, soluble | 0.06 |
| Coriander, soluble | 0.08 |
| White pepper, soluble | 0.06 |
| HVP, Type 3 H1 (hydrolysed vegetable proteins) | 8.90 |
| HVP, Type RF-B (hydrolysed vegetable proteins) | 2.60 |
| Vegetable fat, melting point 40° C. | 17.00 |

| | Parts by weight |
|---|---|
| Roast onion powder | 1.00 |
| | 100.00 | are added to 1 liter of hot water. The flavour of this clear meat soup is initially unsatisfactory (faint meat and onion flavour).

(a) By the addition of 3-5 ppm of 2-(2-pyrazinylethyl)-methyl-disulphide the meat and onion flavour are enhanced in an extremely advantageous manner.

(b) By the addition of 3-5 ppm of 2-pyridyl-propyl-disulphide the meat aroma is enhanced in an advantageous manner in that there now appears a spicy-green note which is reminiscent of chive and which harmonises well with the meat flavour.

EXAMPLE 11

A clear meat broth can be obtained as follows: 20.0 g of a mixture consisting of:

| | Parts by weight |
|---|---|
| Salt | 45.0 |
| Sodium glutamate | 20.0 |
| Sugar | 2.4 |
| Hydrolysed vegetable protein (e.g. HVP, Type 4BE and Type 245) | 14.0 |
| Celery powder | 1.6 |
| Onion powder | 1.6 |
| Garlic powder | 0.6 |
| Curcuma powder | 0.3 |
| Pepper powder, white | 0.1 |
| Potato starch | 4.4 |
| Vegetable fat (melting point 40° C.) | 10.0 |
| | 100.0 | are added to 1 liter of hot water. The flavour of this soup is insipid, weak and not convincing. By the addition of 3-5 ppm of (4,5-dimethyl-2-oxazolyl)-ethyl-disulphide, the weak meat flavour present is significantly strengthened, a pleasant, spicy note reminiscent of roast onions also being obtained, which harmonises excellently with the meat flavour present.

EXAMPLE 12

A meat broth can be obtained as follows: 18.0 g of a mixture consisting of

| | Parts by weight |
|---|---|
| Cooking salt | 45 |
| Monosodium glutamate | 20 |
| Sugar | 2.4 |
| HVP, Type 4 BE(hydrolysed vegetable proteins) | 5.6 |
| HVP, Type 245 (hydrolysed vegetable proteins) | 8.4 |
| Celery powder | 1.6 |
| Onion powder | 2.2 |
| White pepper | 0.4 |
| Carrot starch | 4.4 |
| Hardened vegetable oil | 10 |
| | 100.0 | are added to 1 liter of hot water. The flavour of this meat broth is insipid and not pronounced. By the addition of 2 ppm of 2-(1-methylimidazolyl)-isopropyl-disulphide the meat flavour is enhanced in an advantageous manner. In addition to the pronounced meat note, the thus-obtained meat broth also possesses a pleasant vegetable-like note.

EXAMPLE 13

An exotic fruit flavour can have the composition A or B:

| | A | B |
|---|---|---|
| | Parts by weight | |
| 2-Thiazolyl-butyl-disulphide | — | 1.5 |
| Propylmercaptan (10% in ethyl alcohol) | 2.5 | 1.0 |
| Leaf alcohol (10% in ethyl alcohol) | 1 | 1 |
| α-Pinene | 5 | 5 |
| Isobutyric acid linalyl ester | 5 | 5 |
| Acetic acid amyl ester | 7 | 7 |
| Propionic acid geranyl ester | 10 | 10 |
| Aldehyde C 16 | 12 | 12 |
| Aldehyde C 18 (10% in ethyl alcohol) | 3 | 3 |
| Maltol (2% in ethyl alcohol) | 4 | 4 |
| Aldehyde C 14 | 25 | 25 |
| Garlic oil (0.5% in ethyl alcohol) | 250 | 250 |
| Propyleneglycol | 670.5 | 670.5 |
| | 1000.0 | 1000.0 |

The partial replacement of the propylmercaptan by 2-thiazolyl-butyl-disulphide (composition B) produces a very typical, fruity, sweetish note which is strongly reminiscent of the durian fruit.

EXAMPLE 14

A vegetable flavour can have the composition A or B:

| | A | B |
|---|---|---|
| | Parts by weight | |
| 2-Pyridyl-methyl-disulphide | — | 5 |
| Methylchavicol (1% in ethyl alcohol) | 0.5 | 0.5 |
| Garlic oil | 2.0 | 2.0 |
| Thymol (1% in ethyl alcohol) | 0.5 | 0.5 |
| Isobutyric acid piperonyl ester (1% in ethyl alcohol) | 3 | 3 |
| Nona-2,6-dienal (1% in ethyl alcohol) | 5 | 5 |
| Acetic acid linalyl ester (1% in ethyl alcohol) | 5 | 5 |
| 3-Hexenyl-acetylacetate | 10 | 10 |
| Ethanol | 974 | 969 |
| | 1000 | 1000 |

The presence of 2-pyridyl-methyl-disulphide in composition B enhances the vegetable-like note which is now strongly reminiscent of fresh, green beans.

EXAMPLE 15

A vegetable flavour can have the composition A or B:

| | A | B |
|---|---|---|
| | Parts by weight | |
| 2-(1-Methyl-2-imidazolyl)-propyl-disulphide (10% in ethanol) | — | 10.0 |
| Garlic oil (1°/oo in ethanol) | 2.0 | 2.0 |
| Thymol (1°/oo ethanol) | 0.5 | 0.5 |
| Isobutyric acid piperonyl ester (1°/oo in ethanol) | 3.0 | 3.0 |
| Acetic acid linalyl ester (1% in ethanol) | 5.0 | 5.0 |
| 3-Hexenyl-acetylacetate | 8.0 | 8.0 |
| Methional | 2.0 | 2.0 |
| Ethanol | 979.5 | 969.5 |
| | 1000.0 | 1000.0 |

The odour of the traditional composition A is inferior to the odour of composition B. The addition of 2-(1-methyl-2-imidazolyl)-propyl-disulphide gives a distinctly enhanced, vegetable-like, green note which is reminiscent of fresh green beans.

EXAMPLE 16

An onion flavour can have the composition A or B:

|  | A | B |
|---|---|---|
|  | Parts by weight | |
| 2-Pyrimidinyl-ethyl-disulphide | — | 4.0 |
| Onion oil | 2.0 | 2.0 |
| Onion powder | 400.0 | 400.0 |
| Maltodextrin (in powder form) | 598.0 | 594.0 |
|  | 1000.0 | 1000.0 |

The odour and flavour of an onion powder prepared with composition A are insipid in comparison with an onion powder prepared with composition B. By the addition of 2-pyrimidinyl-ethyl-disulphide the odour and flavour of the onion powder are strongly improved. There appears a distinct, very pleasant novel note in the foreground which is strongly reminiscent of boiled onions.

EXAMPLE 17

An onion flavour can have the composition A or B:

|  | A | B |
|---|---|---|
|  | Parts by weight | |
| 2-Phenylethyl-ethyl-disulphide (0.1% in ethanol) | — | 0.5 |
| Onion oil | 1.0 | 1.0 |
| Ethanol | 10.0 | 10.0 |
| Migliol (neutral oil) | 989.0 | 988.5 |
|  | 1000.0 | 1000.0 |

The comparison of the traditionally insipid flavour A with the novel composition B indicates that the presence of 2-phenylethyl-ethyl-disulphide (composition B) brings about an appreciably enhanced improvement. The impression of boiled onions is only present in composition B.

EXAMPLE 18

An onion flavour can have the composition A or B:

|  | A | B |
|---|---|---|
|  | Parts by weight | |
| (1-Methyl-2-pyrrolyl)-methyl-ethyl-disulphide (10% in ethanol) | — | 5 |
| Onion oil | 20 | 20 |
| Ethanol | 980 | 975 |
|  | 1000 | 1000 |

The odour of the traditional composition A is inferior to that of composition B. By the addition of (1-methyl-2-pyrrolyl)-methyl-ethyl-disulphide the odour is strongly improved. The note reminiscent of boiled onions only appears distinctly in composition B.

EXAMPLE 19

A soya flavour can have the composition A or B:

|  | A | B |
|---|---|---|
|  | Parts by weight | |
| 3-Phenylpropyl-ethyl-disulphide | — | 5 |
| 2,4-Decadienal (10% in ethanol) | 0.8 | 0.8 |
| 2-Hexenal | 10 | 10 |
| Caproic aldehyde | 20 | 20 |
| Dimethylsulphide | 20 | 15 |
| Methional | 40 | 40 |
| Piperidine | 60 | 60 |
| Ethanol | 849.2 | 849.2 |
|  | 1000.0 | 1000.0 |

A comparison of A and B indicates that the traditional composition A falls off odour-wise and flavour-wise. By the partial replacement of the dimethylsulphide by 3-phenylpropyl-ethyl-disulphide there appears a note reminiscent of soya which is very strong in the foreground.

EXAMPLE 20

Mustard flavours (A and B)

|  | A | B |
|---|---|---|
|  | Parts by weight | |
| [2-(4-Methyl-5-thiazolyl)-ethyl]-methyldisulphide | — | 1 |
| Methylchavicol | 2 | 2 |
| Eugenol | 3 | 3 |
| Mace oil | 5 | 5 |
| Thymol (10% in ethanol) | 30 | 30 |
| Mustard oil synthetic | 60 | 60 |
| Ethanol | 900 | 899 |
|  | 1000 | 1000 |

The odour and flavour of the mustard composition A are not very pronounced. On the other hand, by the addition of [2-(4-methyl-5-thiazolyl)-ethyl]-methyldisulphide (composition B) the spicy character is enhanced in an advantageous manner. Moreover, there appears a hot note which is desirable for mustard.

EXAMPLE 21

A horseradish flavour can have the composition A or B:

|  | A | B |
|---|---|---|
|  | Parts by weight | |
| 2-Thiazolyl-isopropyl-disulphide | — | 1.0 |
| Acetic acid | 0.6 | 0.6 |
| Clove oil | 1.0 | 1.0 |
| Mace oil | 1.4 | 1.4 |
| 1-Acetoxy-2-butyl-ethane | 7.0 | 7.0 |
| Mustard oil synthetic | 30.0 | 30.0 |
| Ethanol | 960.0 | 959.0 |
|  | 1000.0 | 1000.0 |

A comparison of composition B with the traditional composition A shows immediately that the latter falls off strongly. By the addition of 2-thiazolyl-isopropyl-disulphide the odour and flavour are substantially improved in that the hot-burning note reminiscent of horseradish appears much stronger in the foreground.

EXAMPLE 22

A garlic flavour can have the composition A or B:

|  | A | B |
|---|---|---|
|  | Parts by weight | |
| Ethyl-thenyl-disulphide (0.1% in ethanol) | — | 0.5 |
| Garlic oil | 1.0 | 1.0 |
| Alcohol | 10 | 10 |
| Tween 80 (Polyoxyethylene sorbitan monooleate) | 30 | 30 |
| Propyleneglycol | 30 | 30 |
| Sorbitol | 35 | 35 |
| Water | 894 | 893.5 |
|  | 1000.0 | 1000.0 |

The odour and flavour of the traditional composition A fall off strongly in comparison with composition B. By the addition of ethyl-thenyl-disulphide the garlic character is significantly improved in that the characteristic sulphur-like, spicy note in the foreground appears only in composition B.

EXAMPLE 23

Mushroom soup (canned soup)
A mixture consisting of:

|  | Parts by weight |
|---|---|
| Skim milk powder | 35 |
| Margarine | 25 |
| White flour | 26 |
| Cooking salt | 5.5 |
| Dried mushroom pieces | 4.5 |
| Natural mushroom aroma | 2.5 |
| Sodium glutamate | 1.6 |
| Onion powder | 0.8 |
| Sugar | 0.4 |
| Pepper flavour, soluble | 0.4 |
| Clove flavour, soluble | 0.3 |
|  | 100.0 | is dissolved in water and boiled up in the usual manner. The flavour of this soup is slightly typical in relation to the mushroom flavour. By the addition of 3-5 ppm of propyl-thenyl-disulphide and mushroom flavour present is activated. The soup has a stronger and fresher flavour. The impression of the co-use of fresh mushrooms is produced.

EXAMPLE 24

A honey flavour can have the composition A or B:

|  | A | B |
|---|---|---|
|  | Parts by weight | |
| 5-Phenylpentyl-ethyl-disulphide | — | 2 |
| Methylacetophenone | 0.5 | 0.5 |
| Geranium oil | 0.3 | 0.3 |
| Ethylvanillin | 6 | 6 |
| Phenylacetic acid | 12 | 12 |
| Pelargonic acid ethyl ester | 30 | 30 |
| Acetic acid amyl ester | 200 | 200 |
| Acetic acid ethyl ester | 100 | 100 |
| Valerianic acid amyl ester | 250 | 250 |
| Ethanol | 401.2 | 399.2 |

-continued

|  | A | B |
|---|---|---|
|  | Parts by weight | |
|  | 1000.0 | 1000.0 |

A comparison of A and B indicates that the traditional composition A falls off strongly. By the addition 5-phenylpentyl-ethyl-disulphide an improvement in the aroma now appears. The ester note is now suppressed and a weak flowery note, which is strongly reminiscent of floral honey, appears in the foreground.

EXAMPLE 23

An odorant substance composition (flowery note) can have the composition A or B:

|  | A | B |
|---|---|---|
|  | Parts by weight | |
| Ethyl-2-(2-furyl)-ethyl-disulphide | — | 5 |
| Methylheptenone | 5 | 5 |
| Linalool | 5 | 5 |
| Acetic acid linalyl ester | 10 | 10 |
| Citronellol | 30 | 30 |
| Geraniol | 40 | 40 |
| Ethanol | 910 | 905 |
|  | 1000 | 1000 |

A comparison of A with B shows immediately that the traditional composition A falls off strongly. By the addition of ethyl-2-(2-furyl)-ethyl-disulphide the flowery-green note of the composition is enhanced. It is intensively reminiscent of geranium.

What we claim is:

1. A process for making disulfides having the formula:

$$R_1-(Y)_n-S-S-R_2$$

which process comprises reacting in an inert solvent at a temperature between $-20°$ C. and $50°$ C. a sulfonium salt of the general formula:

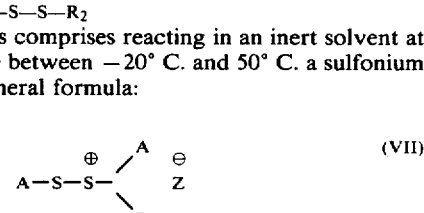

with the mercaptan of the general formula:

$$A-SH \quad \text{(VIII)}$$

whereby in the one reaction component A represents a group $R_1(Y)_n$ and in the other reaction component A represents a group $R_2$; $R_1$ is an optionally $C_{1-6}$ alkyl-substituted phenyl or furyl group or an optionally $C_{1-6}$ alkyl-substituted, 5-membered or 6-membered heterocyclic group which contains one or more nitrogen atoms and/or one or more sulfur atoms; Y is an optionally mono- or di-$C_{1-6}$-alkyl or $C_{2-6}$-alkenyl-substituted mono- or di-substituted methylene group, n stands for 0–5 with the proviso that n stands for 2–5 when $R_1$ represents the phenyl or furyl group, $R_2$ represents a lower alkyl or alkenyl group containing up to 6 carbon atoms; R represents a $C_{1-6}$-alkyl group and $Z^\ominus$ represents an anion selected from the group consisting of tri (lower alkyl) oxonium salt, hexachloroantimonate, perchlorate, nitrate, arylsulphonate and alkyl sulphonate.

* * * * *